US008620690B2

(12) United States Patent
Hu et al.

(10) Patent No.: US 8,620,690 B2
(45) Date of Patent: Dec. 31, 2013

(54) ASSESSING PRACTITIONER VALUE IN MULTI-PRACTITIONER SETTINGS

(75) Inventors: Jianying Hu, Bronx, NY (US); Fei Wang, Ossining, NY (US); Robert K. Sorrentino, Rancho Palos Verdes, CA (US); Shahram Ebadollahi, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 124 days.

(21) Appl. No.: 13/312,685

(22) Filed: Dec. 6, 2011

(65) Prior Publication Data
US 2013/0144639 A1 Jun. 6, 2013

(51) Int. Cl.
*G06Q 50/00* (2012.01)
*G06Q 50/22* (2012.01)

(52) U.S. Cl.
CPC ..................... *G06Q 50/22* (2013.01)
USPC ............. 705/3; 705/7.39; 705/7.41; 705/7.42

(58) Field of Classification Search
USPC ........................ 705/2–4, 7.11–7.42
See application file for complete search history.

(56) References Cited

U.S. PATENT DOCUMENTS

| | | | |
|---|---|---|---|
| 5,724,379 A * | 3/1998 | Perkins et al. ............. | 705/2 |
| 5,924,073 A | 7/1999 | Tyuluman | |
| 6,338,042 B1 * | 1/2002 | Paizis ......................... | 705/7.37 |
| 7,444,291 B1 | 10/2008 | Prasad | |
| 8,165,894 B2 * | 4/2012 | Tawil .......................... | 705/2 |
| 2006/0241974 A1 | 10/2006 | Chao | |
| 2007/0078680 A1 | 4/2007 | Wennberg | |
| 2008/0133290 A1 | 6/2008 | Siegrist, Jr. | |
| 2008/0262882 A1 | 10/2008 | Farrell | |
| 2009/0259488 A1 * | 10/2009 | Gounares et al. ............. | 705/3 |
| 2010/0169119 A1 * | 7/2010 | Hussain ........................ | 705/3 |
| 2010/0274580 A1 * | 10/2010 | Crownover et al. ........... | 705/2 |
| 2010/0305964 A1 | 12/2010 | Eddy | |
| 2012/0109683 A1 * | 5/2012 | Ebadollahi et al. ........... | 705/3 |

OTHER PUBLICATIONS

Klabunde, C. N., Keating, N. L., Potosky, A. L., Ambs, A., He, Y., Hornbrook, M. C., & Ganz, P. A.A population-based assessment of specialty physician involvement in cancer clinical trials. Journal of the National Cancer Institute, 103(5), 384-397. doi:http://dx.doi.org/10.1093/jnci/djq549.*

(Continued)

*Primary Examiner* — Mark Holcomb
(74) *Attorney, Agent, or Firm* — Louis J. Percello; Otterstedt, Ellenbogen & Kammer, LLP

(57) ABSTRACT

A plurality of actual outcome data points, including actual outcomes for a plurality of episodes of a process, are obtained for the process. A practitioner-independent baseline outcome is also obtained for the process. For each given one of the actual outcome data points, the given one of the actual outcome data points is equated to the practitioner entity-independent baseline outcome multiplied by a plurality of unknown participating practitioner entity outcome indices for each of a plurality of participating practitioner entities. Each of the participating practitioner entity outcome indices is raised to an exponent including a corresponding one of a plurality of unknown participating practitioner entity type indices, to obtain a plurality of equations. The plurality of equations are solved to obtain estimated values of the unknown participating practitioner entity outcome indices and estimated values of the unknown participating practitioner entity type indices.

22 Claims, 4 Drawing Sheets

(56) References Cited

OTHER PUBLICATIONS

Susan E. Pantely, "Whose patient is it? Patient attribution in ACOs," Milliman Healthcare Reform Briefing Paper, 2010.
Pacific Business Group on Health Report, Advancing Physician Performance Measurement: Using Administrative Data to Assess Physician Quality and Efficiency, 2005.
Physician Consortium for Performance Improvement, http://www.ama-assn.org/ama/pub/physician-resources/clinical-practice-improvement/clinical-quality/physician-consortium-perfo.
Carl Bacon, Evaluation of Performance Attribution Methodologies, presentation at "Performance Attribution" round table, 2004.
Ben Recht. Projected Gradient Methods. Notes for course Nonlinear Optimization I, Fall 2010. from http://pages.cs.wisc.edu/~brecht/cs726docs/ProjectedGradientMethods.pdf.

* cited by examiner

THE MULTIPLICATIVE REGRESSION MODEL:

MODEL ESTIMATED LOS 202
EXPECTED LOS 204
POI OF THE CARDIOLOGIST 206
POI OF THE RENAL SPECIALIST 208

$$\hat{O}_i = a_i \times s_{c_i} \times s_{r_i} \quad\quad c_i \in \{C1, C2\},\ r_i \in \{R1, R2\}$$

200          210

300 {
PRACTITIONER C1 TENDS TO DECREASE LOS BY 10%
PRACTITIONER C2 TENDS TO DECREASE LOS BY 20%

$a_i = 6.9,\quad S_{C1} = 1.1,\ S_{C2} = 0.8,\ S_{R1} = 0.6,\ S_{R2} = 1.5$
}

302 {

| | | | | | |
|---|---|---|---|---|---|
| C1, R1 | 4 (0.5) | 4 (0.5) | 5 (−0.5) | 5 (−0.5) | 4.5 |
| C1, R2 | 11 (0.4) | 12 (−0.6) | | | 11.4 |
| C2, R1 | 3 (0.3) | 4 (−0.7) | | | 3.3 |
| C2, R2 | 8 (0.3) | 9 (−0.7) | 9 (−0.7) | 9 (−0.7) | 8.3 |

}

MODEL PREDICTED LOS

FIG. 4

$$o_i = \overbrace{a_i}^{402} \underbrace{s_{i_1}^{\beta_{i_1}} s_{i_2}^{\beta_{i_2}} \cdots s_{i_{k_i}}^{\beta_{i_{k_i}}}}_{406}$$

401 → $o_i$  402 → $a_i$  400 (overbrace)

$$\underbrace{f^*(x_i) = \arg\min_f \sum_i \overbrace{\boxed{\mathcal{L}(f(x_i), o_i)}}^{451}}_{404}$$

$$\min_{\{\log s_j\}_{j=1}^{K}, \{\beta_m\}_{m=1}^{M}} \overbrace{\sum_{i=1}^{N} \left[\log o_i - \left(\log a_i + \sum_{j \in \mathcal{P}_i} \beta_j \log s_j\right)\right]^2}^{599}$$

FIG. 6

$$\min_{\{\log s_j\}_{j=1}^{K}} \overbrace{\sum_{i=1}^{N} \left[\log o_i - \left(\log a_i + \sum_{j \in \mathcal{P}_i} \log s_j\right)\right]^2}^{699}$$

ASSESSING PRACTITIONER VALUE IN MULTI-PRACTITIONER SETTINGS

STATEMENT OF GOVERNMENT RIGHTS

Not Applicable.

CROSS-REFERENCE TO RELATED APPLICATIONS

Not Applicable.

FIELD OF THE INVENTION

The present invention relates to the electrical, electronic and computer arts and more particularly, to informatics and the like.

BACKGROUND OF THE INVENTION

Services, such as health care services, are often delivered by multiple practitioners, particularly in the case of healthcare services for patients with complex conditions. In some instances, multiple specialists collectively care for a patient with multiple co-morbidities, and a team of practitioners (surgeon, anesthesiologist, etc.) collectively provide service to a surgery patient.

The ability to assess each practitioner's value based on outcomes of care in such settings is important for effective care management and care improvement. It is a very challenging task since it is not straightforward to attribute the outcome of a collaborative effort to individual practitioners. This is particularly true since most of the time actions and degree of effort of each practitioner are not routinely recorded.

Currently, heuristic methods are used to attribute or assign patients (episodes) to practitioners. For example, in a single designation approach, the patient/episode is assigned to the practitioner who has seen the patient most in a multiple designation approach, assignment is based on the frequency or accumulated duration of visits.

SUMMARY OF THE INVENTION

Principles of the invention provide techniques for assessing practitioner value in multi-practitioner settings. In one aspect, an exemplary method includes the steps of obtaining a plurality of actual outcome data points comprising actual outcomes for a plurality of episodes of a process; obtaining a practitioner-independent baseline outcome for the process; for each given one of the actual outcome data points, equating the given one of the actual outcome data points to the practitioner entity-independent baseline outcome multiplied by a plurality of unknown participating practitioner entity outcome indices for each of a plurality of participating practitioner entities, each of the participating practitioner entity outcome indices being raised to an exponent comprising a corresponding one of a plurality of unknown participating practitioner entity type indices to obtain a plurality of equations; and solving the plurality of equations to obtain estimated values of the unknown participating practitioner entity outcome indices and estimated values of the unknown participating practitioner entity type indices.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

- assigning an outcome index (impact factor) to each practitioner;
- the outcome indices have intuitive interpretation;
- allows consideration of different degree impact by different types of practitioners;
- indices can be derived from observational data using mathematically sound methods; and
- the methodology also provides outcome indices for teams of practitioners.

These and other features and advantages of the present invention will become apparent from the following detailed description of illustrative embodiments thereof, which is to be read in connection with the accompanying drawings.

BRIEF DESCRIPTION OF THE DRAWINGS

FIG. 4 shows an exemplary formulation of a practitioner outcome index (POI) model, according to an aspect of the invention;

FIG. 5 shows an exemplary illustration of a model estimation method, according to an aspect of the invention;

FIG. 6 shows a special case of POI model estimation, when all PTIs (practitioner type indices) are set to unity, according to an aspect of the invention;

DETAILED DESCRIPTION OF PREFERRED EMBODIMENTS

Figure 1:
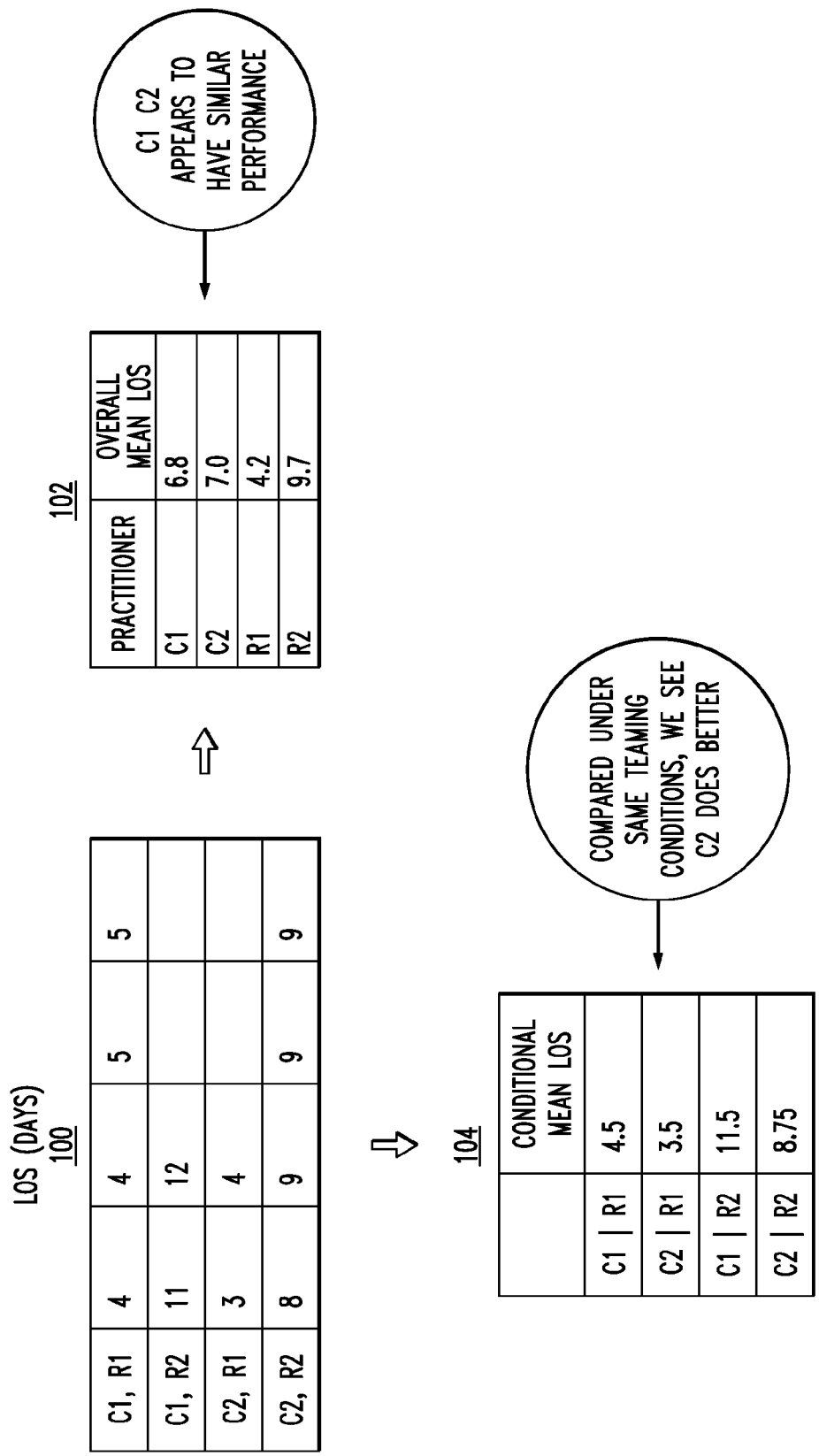
FIG. 1 shows an exemplary scenario of outcome attribution in a multi-practitioner setting, according to an aspect of the invention.

As noted, services such as healthcare services are often delivered by multiple practitioners, particularly in the case of healthcare services for patients with complex conditions. For example, multiple specialists collectively care for a patient with multiple co-morbidities, and/or a team of practitioners (surgeon, anesthesiologist, etc.) collectively provide service to a surgery patient.

Being able to assess each practitioner's value based on outcomes of care in such settings is important for effective care management and care improvement. It is a very challenging task since it is not straightforward to attribute the outcome of a collaborative effort to individual practitioners. This is particularly true since most of the time, actions and degree of effort of each practitioner are not routinely recorded.

It should be noted that embodiments of the invention are suitable for, but not limited to, healthcare performance evaluation. Other non-limiting examples of applications include any situation where outcome is driven by contributions from multiple practitioners, such as evaluation of legal team performance, evaluation of an information technology (IT) engagement, and so on.

Currently, heuristic methods are used to attribute or assign patients (episodes) to practitioners. In a single designation approach, the patient/episode is assigned to the practitioner who has seen the patient most in a multiple designation approach, assignment is based on the frequency or accumulated duration of visits.

One or more embodiments advantageously provide a comprehensive and consistent model for practitioner evaluation in the multi-practitioner setting. One or more instances include techniques for performance evaluation by modeling the outcome as the function of a practitioner-independent baseline outcome and a set of individual practitioner outcome indices (POIs) and practitioner type indices (PTTs).

One or more embodiments include one, some, or all of the following advantages: (i) assigning an outcome index (impact factor) to each practitioner; (ii) the outcome indices have intuitive interpretation; (iii) allows consideration of different degree impact by different types of practitioners; (iv) indices can be derived from observational data using mathematically sound methods; and (v) the methodology also provides outcome indices for teams of practitioners.

One or more embodiments relate to assessing practitioner value based on observed outcomes of a collection of healthcare (or other) episodes (or evaluation period) provided by a set of practitioners, potentially of different types, and potentially in different team combinations. Specifically, one or more embodiments provide a model, referred to herein as the POI model, wherein the outcome of an episode is the function of a baseline outcome, a set of parameters called "practitioner outcome indexes" (POI), and a set of parameters called "practitioner type indices" (PTI). The baseline outcome represents the expected outcome for the patient, and is derived using factors independent of who provided the care (e.g., patient characteristics, environmental factors, hospital characteristics, and the like). One presently preferred way to compute the baseline outcome is through regression, where outcome is the dependent variable, and the independent variables include all non-practitioner-specific factors. Another way to compute the baseline outcome is by averaging over all patient episodes with common non practitioner specific characteristics.

The POI of a practitioner is a positive number, with POI<1 indicating the practitioner tends to lower the outcome measure, and POI>1 indicating the practitioner tends to increase the outcome measure. The PTI of a practitioner type (e.g., cardiologist, nurse coordinator, etc.) indicates the degree of impact of a particular practitioner type (i.e., which practitioner type is more significant for a particular condition and outcome). The PTIs can be defined by experts or inferred from data. If the PTI of a practitioner type is 1, then POI=1.1 for a practitioner of that type can be interpreted as: the practitioner tends to increase the outcome by 10%. For outcome measures where higher numbers are more desirable, higher POI indicates better performance; for outcome measures where lower numbers are more desirable, lower POI indicates better performance.

In one or more embodiments, the function is a multiplicative regression model.

The model can, in some instances, also be formulated to evaluate the index of a specific combination (team) of practitioners, by treating a team as a practitioner.

One or more instances provide a method to derive PTIs and POIs for a set of practitioners using a set of observed episodes, such that the POIs and PTIs provide the best explanation for the observed outcome (double linear regression). The method can be repeated over any time or at regular interval, to obtain updated POI and PTI values, and to track the performance evolution of individuals and teams. In one embodiment, the model can be run after an episode stratification process, where episodes are segmented based on patient characteristics and/or types of practitioners involved.

An exemplary overview of an embodiment of the POI model will now be provided. A goal of one or more embodiments is to evaluate performance of each practitioner, while taking into account the possible effect of other practitioners, and also controlling for patient and other characteristics, for a given outcome measure. In one or more instances, the approach is as follows. The practitioner outcome index model infers a Practitioner Outcome Index (POI) that captures the general performance level of a practitioner over an observation period with regard to a specific outcome, in comparison to other practitioners observed in the same period. A value of POI=1 indicates average performance; a value of POI>1 indicates above average performance; and a value of POI<1 indicates below average performance (or the reverse, depending on the nature of the outcome measure).

The POI model is able to directly answer the question of over a given evaluation period, based on observed episodes and outcomes, which practitioners tend to have positive effect on patient outcome, which ones have negative effect on patient outcome, and by how much.

The POI model is able to indirectly answer the question of for example, given a patient with an adverse outcome, where 17 different physicians touched the patient, which physicians are mostly likely responsible for the adverse outcome. In such a case, based on track record, the providers with the lowest Practitioner Outcome Indices (POIs) are most likely responsible for the adverse outcome. It should be noted that the model cannot definitively identify who is responsible for the adverse outcome, but can infer the "most likely" practitioners to have been responsible, based on track record.

Attention should now be given to FIG. 1 for an illustrative example of a POI model. Cases of hospitalization involving a cardiologist ("C") and a renal specialist ("R") are considered. Stratification is carried out based on the types of providers involved, assuming the Provider Type Indices for both specialists are 1. Length of stay (LOS) is used as the outcome. LOS is one of many possible measurements of outcome and is chosen for illustrative purposes. Assume all involved patients have been stratified by risk conditions (in an alternative embodiment this can be handled via a baseline regression model instead of matching). Furthermore in this regard, consider the parameter $a_i$ (designated as 204 in FIG. 2 and 402 in FIG. 4), which represents the baseline or average expected outcome for the specific patient. There are several ways to arrive at this expected outcome. In one aspect, patent stratification by risk conditions is employed; i.e., pre-segment patients into groups by risk factors and take an average for each group. This results in a baseline outcome that is reasonable for the given patient; that is to say, a better outcome is expected for a patient who is relatively less sick and a worse outcome is expected for a patient who is relatively sicker. For example, suppose Disease X has three levels of severity based on a variety of symptoms and other factors; it might be determined that patients in the least severe category are expected to remain in the hospital one week on average; those with moderate severity typically remain for 1.5 weeks on average; and those with the worst level of severity are expected to remain for five weeks on average. In another aspect, a regression model is employed wherein, given the pertinent characteristics of a given patient, the regression model will determine an expected outcome for the patient. Suitable regression techniques, in and of themselves, are known to the skilled artisan and can be adapted to one or more embodiments of the invention, given the teachings herein.

Now, assume two cardiologists C1, C2, and two renal specialists, R1, R2 were observed in these cases, with LOS shown in table 100. It is desired to determine how each provider performed. Table 102 tabulates the overall mean LOS for each practitioner. It is noted that C1 and C2 appear to have similar performance, 6.8 versus 7.0. Table 104 tabulates the conditional mean LOS. Here, it can be seen that under the same teaming conditions, C2 performs better than C1; 3.5 versus 4.5 when working with R1 and 8.75 versus 11.5 when working with R2. One or more embodiments advantageously make this type of inference systematic and scalable.

Figures 2, 3:
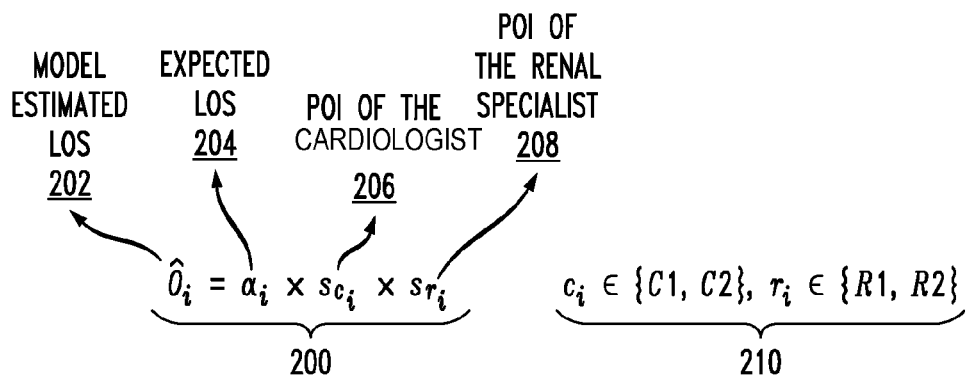
FIG. 2 shows a multiplicative regression model of the exemplary POI model, according to an aspect of the invention.
FIG. 3 shows an exemplary optimal solution of the exemplary POI model, according to an aspect of the invention.

Referring now to FIG. 2, note the multiplicative regression model 200. Here for illustrative purposes, make the simplifying assumption that the PTI for both practitioner types (cardiologist and renal specialist) is 1. The "hat" over $O_i$ indicates a model-predicted outcome for patient i. One or more embodiments seek to minimize the difference between the model-predicted and actual outcomes, when summed over all observed cases by solving the corresponding optimization problem. The model-estimated LOS 202 is given by the product of the expected LOS 204, the POI of the cardiologist 206, and the POI of the renal specialist 208. The ranges of the subscripts are shown at 210. In the case of LOS for the example of FIG. 2, the higher the number, the worse the outcome; thus, here, POI>1 is undesirable and POI<1 is desirable. The expected LOS 204 is a baseline outcome based on practitioner-independent factors. As noted above, the baseline outcome represents the average outcome over all practitioners, and is derived using factors independent of who provided the care (e.g., patient characteristics, environmental factors, hospital characteristics, and the like). Again, as noted above, one way to compute the baseline outcome is by averaging over all patients with certain characteristics; another way to compute the baseline outcome is through regression, where outcome is the dependent variable, and the independent variables include all non-practitioner-specific factors. See also further discussion below.

Referring now to FIG. 3, the optimal solution is the one that minimizes the regression error, providing the best explanation of observed outcomes under the model. As seen at 300, the expected LOS is 6.9; the POI for cardiologist C1 is 1.1; that for cardiologist C2 is 0.8; that for renal specialist R1 is 0.6; and that for renal specialist R2 is 1.5. The values 1.1, 0.8, 0.6, and 1.5 are determined by minimizing the difference between the model-predicted outcome and the actual outcome. For each patient i there is an actual (observed) outcome, and the indices are estimated based on observed data. The goal is to solve for the indices in a way such that use of the indices minimizes the difference between the model-predicted outcome and the actual outcome. The values of 1.1, 0.8, 0.6, and 1.5 are the result of solving for that optimization problem.

Thus, cardiologist C1 tends to increase LOS by 10% while cardiologist C2 tends to decrease LOS by 20%, as indicated by the respective POI values 1.1, 0.8. Table 302, in the first five columns, repeats the data of table 100 and adds in parentheses the difference of each individual data point from the model-predicted value. The last (sixth) column is the model-predicted LOS, from equation 200, for each of the four practitioner combinations.

By way of review and provision of additional detail, in the example of table 100, assume the following conditions:

Cases of hospitalization involving a Cardiologist (C) and a Renal specialist (R).

There are two cardiologists C1, C2, and two renal specialists, R1, R2, which are observed in these cases.

The PTI for both practitioner types (cardiologist and renal specialist) is 1.

To apply an exemplary technique, according to an aspect of invention, first compute the average length of stay as:

$$\alpha=(4+4+5+5+11+12+3+4+8+9+9+9)/12=6.9 \tag{1}$$

Assuming that the factors for $C_1, C_2, R_1, R_2$ that it is desired to solve are $S_{C1}, S_{C2}, S_{R1}, S_{R2}$, then the following equation group is obtained:

$$\log \alpha + \log S_{C1} + \log S_{R1} = \log 4 \tag{2}$$

$$\log \alpha + \log S_{C1} + \log S_{R1} = \log 4 \tag{3}$$

$$\log \alpha + \log S_{C1} + \log S_{R1} = \log 5 \tag{4}$$

$$\log \alpha + \log S_{C1} + \log S_{R1} = \log 5 \tag{5}$$

$$\log \alpha + \log S_{C1} + \log S_{R2} = \log 11 \tag{6}$$

$$\log \alpha + \log S_{C1} + \log S_{R2} = \log 12 \tag{7}$$

$$\log \alpha + \log S_{C2} + \log S_{R1} = \log 3 \tag{8}$$

$$\log \alpha + \log S_{C2} + \log S_{R1} = \log 4 \tag{9}$$

$$\log \alpha + \log S_{C2} + \log S_{R2} = \log 8 \tag{10}$$

$$\log \alpha + \log S_{C2} + \log S_{R2} = \log 9 \tag{11}$$

$$\log \alpha + \log S_{C2} + \log S_{R2} = \log 9 \tag{12}$$

$$\log \alpha + \log S_{C2} + \log S_{R2} = \log 9 \tag{13}$$

Let:

$$s = [S_{C_1}, S_{R_1}, S_{C_2}, S_{R_2}] \quad (14)$$

and $$A = \begin{bmatrix} 1 & 1 & 0 & 0 \\ 1 & 1 & 0 & 0 \\ 1 & 1 & 0 & 0 \\ 1 & 1 & 0 & 0 \\ 1 & 0 & 0 & 1 \\ 1 & 0 & 0 & 1 \\ 0 & 1 & 1 & 0 \\ 0 & 1 & 1 & 0 \\ 0 & 0 & 1 & 1 \\ 0 & 0 & 1 & 1 \\ 0 & 0 & 1 & 1 \\ 0 & 0 & 1 & 1 \end{bmatrix} \quad (15)$$

and $$b = [\log 4, \log 4, \log 5, \log 5, \log 11, \log 12, \log 3, \log 4, \log 8, \log 9, \log 9, \log 9]^T - \log 6.9 \quad (16)$$

Then the estimate of s can be obtained by:

$$\hat{s} = (A^\top A)^\dagger A^\top b = \begin{bmatrix} 1.0881 \\ 0.5975 \\ 0.8352 \\ 1.5210 \end{bmatrix} \quad (17)$$

where the dagger symbol represents the pseudo inverse.

FIG. 4 depicts formulation of the POI model. The episode is patient hospitalization for congestive heart failure (CHF). As per equation 400, the outcome 401 is LOS. The baseline outcome 402 is based on practitioner-independent factors and is calculated as shown at 404. Equation 400 is a more general form of the equation in FIG. 2, and equation 404 shows the regression model for estimating $a_i$. The parameter $a_i$ is the same as defined above. The parameter $o_i$ is the actual outcome for the $i^{th}$ patient (patient episode i). There are $k_i$ participating practitioners for patient episode i. Each practitioner has a participating practitioner outcome (POI) index $S_{i1}, S_{i2},$ and so on.

Furthermore, practitioners will typically be of different types; say, cardiologists and primary care physicians. Different types of physicians may have a different degree of impact on patient outcome. This aspect is captured in FIG. 4 by the additional parameters $\beta_{i1}, \beta_{i2} \ldots$ (participating practitioner type indices). The $S_{i1}, S_{i2},$ factors are being raised to the $\beta_{i1}, \beta_{i2}$, powers. The practitioner independent factors $x_i$ are designated as 453 and the loss function is designated as 451.

Now the $s_j$ and $\beta_j$ factors are solved for simultaneously via bilinear least square regression in FIG. 5 (bilinear least squares regression with square loss 599). Here, there is no closed form solution and an iterative approach, using gradient descent or the like, can be employed.

The LOS 401 is predicted as the baseline outcome 402 multiplied by the POI values for each practitioner associated with the treatment of patient i (here, a total of k practitioners), each raised to the power of the corresponding $\beta_{i1}, \beta_{i2}$, as seen at 406. Referring to block 404 in FIG. 6, the $x_i$ values 453 are practitioner-independent patient characteristics, e.g., age, gender, blood pressure level, latest diagnosis, and so on (physical parameters having nothing to do with the doctor but rather with the level of health/sickness of the patient and other patient parameters). The parameter $f^*$ represents a functional form—many different types of regression functions can be used to estimate $a_i$, but in every case the goal is to find the model parameters that will result in the minimal loss function as seen on the right-hand side of equation 404. The goal is to compare the predicted value from the function $f(x_i)$ against the actual value $o_i$ and minimize the loss. In some cases, a least squares approach is employed; i.e., minimize the square of the differences and employ a linear regression. The goal of the regression process is to search through a function space of functions $f$ to locate the function $f^*$ that minimizes the loss.

Now there are a set of equations in the following form (equivalent to equation 400 in FIG. 4):

$$o_i = a_i s_{i_1}^{\beta_{i_1}} s_{i_2}^{\beta_{i_2}} \ldots s_{i_{k_i}}^{\beta_{i_{k_i}}} \quad (18)$$

Taking the logarithm on both sides, obtain:

$$\log o_i = \log a_i + \sum_{j=1}^{k_i} \beta_{i_j} \log s_{i_j} \quad (19)$$

Then the problem to be optimized becomes:

$$\min_{\beta, s} \sum_{i=1}^{n} \left[ \log o_i - \left( \log a_i + \sum_{j=1}^{k_i} \beta_{i_j} \log s_{i_j} \right) \right]^2 \quad (20)$$

$$\text{s.t. } \beta \geq 0 \quad (21)$$

Since the objective is quadratic with respect to β and s, an alternating optimization approach can be adopted for solving the problem. First, initialize all the elements in β to 1, and then solve the optimal s vector by regular least square which has a closed form solution; then fix s, and solve the optimal β via projected gradient descent. The procedure will iterate until convergence.

FIG. 5 depicts an exemplary model estimation method; in particular, an exemplary non-limiting manner of solving equation 400 by taking logarithms so that the multiplications in equation 400 become summations. K is the number of distinct practitioners, M is the number of distinct practitioner types, 599 is the square loss, and $P_i$ is the collection of practitioners participating in patient episode i. The log $o_i$ is the log of the actual outcome and the term in parentheses is the (log) model-estimated outcome. The goal is to minimize the square of the difference between the two and the end result is a value for all of the $s_j$ and $\beta_j$ terms. The skilled artisan will appreciate that FIG. 5 illustrates an application of bilinear least-squares regression.

FIG. 6 illustrates a special case of the model of FIGS. 4 and 5, wherein one can assume that all practitioner types have equal impact (i.e., all β parameters have a value of 1 because all practitioner types have equal impact). The square loss is at 699. Compare to equation 17 above. Note that squared error is one non-limiting example of a loss function and it has a closed form solution; for functions where no closed form solution is available, use an iterative approach such as gradient descent to solve the optimization problem.

It is believed that use of Practitioner Type Impact factors is useful in medical applications. For medical applications, depending on the condition being treated and the outcome being measured, it is expected that different types of practitioners have different degrees of impact over the outcome (e.g., a cardiologist may have bigger impact than a nutritionist for a CHF patient). The use of PTIs insures that each practitioner of a particular type is compared against his or her peers (that is, a cardiologist is not compared against a nurse in deriving the outcome index). This may also be significant in other domains; for example, in a law suit, one would expect the impact of the lead attorney to be higher than the impact of an assistant.

With regard to the expected (or baseline) outcome based on practitioner independent factors, at present, it is believed that use of the regression model 404 in FIG. 4 is preferred, because this gives a more patient specific and thus more accurate baseline estimate. An alternative, simpler approach is to use the average over a group of patients that are considered to be similar enough. This again can be considered a special case of the regression model, when the regression coefficient for all independent variables is set to 0.)

Note that in the example of FIGS. 1 and 2, in order to illustrate the concept using a simple example, the simplifying assumptions listed above were used. In particular, assume all betas (in this example there are two, one for the cardiologist, one for the renal specialist) are 1 (i.e., each practitioner type has equal impact), and also assume that all patients in these 12 cases have the same physician independent characteristics and therefore the same $a_i$ (i.e., average of all cases).

It should be noted that this example is for illustrative purposes, it does not encompass all aspects of the full model as defined by equation 400. The full model of FIG. 4 can be estimated using the optimization equation of FIG. 5 (solvable via bilinear least square regression), and using the equation of FIG. 6 in the special case when the betas are set to 1 (solvable using linear least square regression).

Expressions 18-21 describe the detailed steps of the bilinear least square regression process for estimating the POI model. Note that the "regular least square" step is described in equations 1-17. The "projected gradient descent" mentioned below equations 20 and 21 is a standard technique that is explained in many text books. One such book is Dimitri P. Bertsekas, Nonlinear Programming: 2nd Edition, Athena Scientific, 1999, expressly incorporated herein by reference in its entirety for all purposes. Given the teachings herein, the skilled artisan will be able to adapt known projected gradient descent techniques, or other techniques, to implement one or more embodiments.

Figure 7:
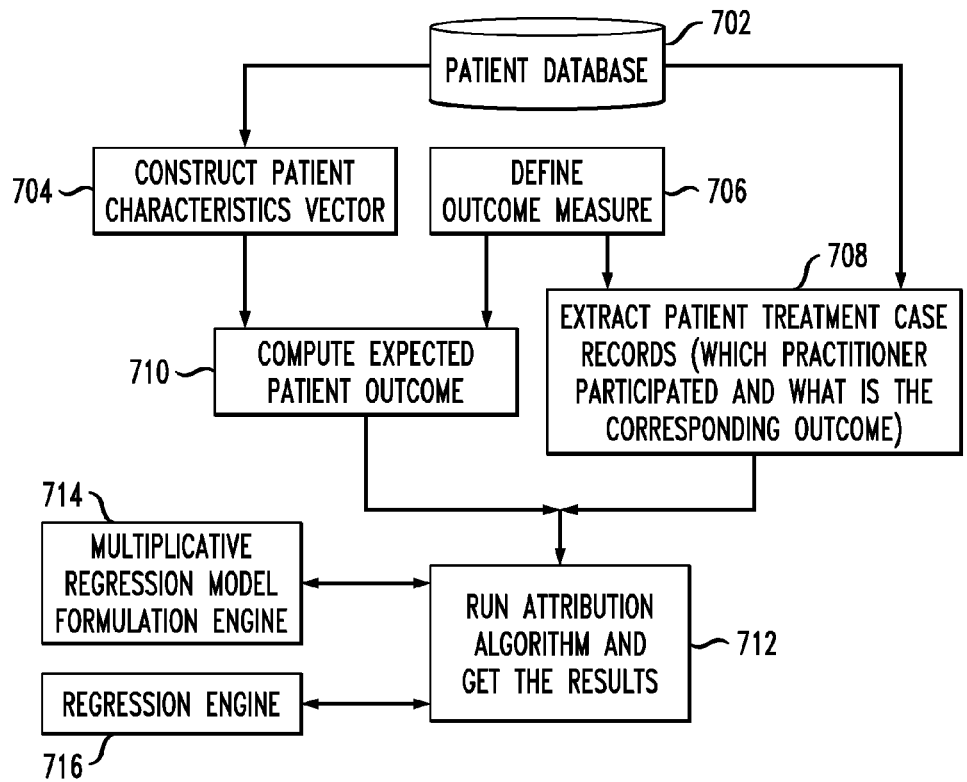
FIG. 7 is a combined flow chart and software architecture diagram, according to an aspect of the invention.

FIG. 7 presents an exemplary combined block diagram and flow chart. Patient database 702 includes records of patients, which practitioners treated those patients, and what the outcome was. There may be more than one outcome measure, e.g., LOS, whether the patient needed to be treated again within a given time period (e.g., 30 day readmission rate), length of survival, and so on. Step 704 includes conversion of raw patient data (e.g., encounter records specifying that a given patient was seen on a given date, what the diagnosis was, what the lab results were, and so on) into feature values that can be used to characterize a patient. For example, suppose the patient had multiple blood pressure readings in the last six months. A determination is made as to how to represent same; e.g., average of all readings over six months is a representation of the patient's general state; the trend of the blood pressure readings in time might also be useful as a feature. Step 704 is preferably automated, although the underlying logic for the type of conversions to be performed may be programmed with the aid of a human expert. In some instances, step 704 can be implemented using a suitable query engine which queries database 702. One non-limiting example of suitable software is IBM's DB2® database software available from International Business Machines Corporation, Armonk, N.Y., USA. In some cases, the engine is sufficiently sophisticated such that the queries also carry out the calculations; in other instances, the queries take the raw data and feed same into a spreadsheet or statistics program to carry out the calculations.

Step 706 includes a human expert selecting and inputting the appropriate outcome measure: again, LOS, whether the patient needed to be treated again within a given time period, length of survival, and so on. In step 710, the expected patient outcome $a_i$ is calculated by a suitable software module as described above (regression or averaging) referred to herein as a baseline outcome computation module. The box for step 710 is equally indicative of such a module in a block diagram. In step 708, the actual outcome and actual participating practitioner(s) are extracted from the database 702, again using a suitable database query engine to query database 702. In step 712, the attribution algorithm is run and the results obtained; in particular the equations of FIGS. 4, 5, and 6 are solved as appropriate (depending on whether practitioner typing is to be taken into account). Step 712 may be carried out, for example, using a multiplicative regression model formulation engine 714 to form the matrices corresponding to multiple instances of equation 400 (e.g., equations 2-13 in the above simplified example), and also using a suitable regression engine 716 to solve 599 (or 699 in the simplified case).

One or more embodiments thus advantageously provide methods for practitioner evaluation, especially in cases of multiple practitioner involvement; in at least some cases, techniques are provided for assigning performance indexes to individual practitioners in a multi-practitioner setting and/or to attribute outcomes to different practitioners.

One or more embodiments advantageously provide a method and system for assessing practitioner value based on the outcomes of cases: particularly wherein each case involves at least one practitioner. One or more embodiments include a model, called the Practitioner Outcome Index (POI) model, which represents the outcome of each case as a function of the Practitioner Outcome Index of each practitioner who worked on the case. In at least some instances, the function further includes a baseline outcome.

The baseline outcome represents the average outcome over all practitioners, and is derived using factors independent of who participated in the case (i.e., patient characteristics, environmental factors, hospital characteristics, and the like). One way to compute the baseline outcome is by averaging over all patients with certain characteristics. Another way to compute the baseline outcome is through regression where outcome is the dependent variable, and the independent variables include all non-practitioner-specific factors.

In at least some instances, the POI of a practitioner is a positive number, with POI≥1 indicating the practitioner tends to lower the outcome measure, and POI>1 indicating the practitioner tends to increase the outcome measure. For example, POI=1.1 can be interpreted as the practitioner tends to increase the outcome measure by 10% compared to baseline.

One embodiment includes a multiplicative model.

Some instances provide a method to derive POIs for a set of practitioners using a set of observed episodes, such that the POIs provide the best explanation of the observed outcome. A preferred approach further includes a set of factors called "practitioner type impact" (PTI) factors. A PTI indicates the degree of impact of a particular practitioner type (i.e., which practitioner type is more significant for a particular condition and outcome).

One or more embodiments further provide a method to derive PTIs along with POIs using a set of observed episodes, such that the PTIs provide the best explanation for the observed outcome. The model can also be formulated to evaluate the index of a specific combination (team) of providers. The method can be repeated over any time or at regular intervals, to obtain updated POI and PIT and to track the performance evolution of individuals and teams.

One or more embodiments of the invention thus broadly provide a Practitioner Value Assessment Tool, capable of rating and/or ranking groups and/or individuals in groups (in particular medical professionals) in their contribution to an outcome of a project (patient well being) where each individual has a different skill set and contributes to a different part of the project.

In addition to evaluating medical professionals, one or more embodiments can be used to evaluate other kinds of professionals; for example, members of a team of legal professionals working on a litigation. The outcomes could be, for example, whether the litigation was won or lost, and the amount of damages (if any). The relative merits of the case are the practitioner-independent parameters analogous to the patient's underlying state of health. In the case of an engineering team constructing a bridge over a high gorge, the outcomes could be cost, construction time, construction safety, how long the bridge will last with proper maintenance, and so on. The topography, soil conditions, seismic conditions, wind conditions, and the like are the practitioner-independent parameters, analogous to the patient's underlying state of health. Furthermore, some embodiments of the invention can be directed to inanimate actors such as components of a technological system. Expensive technological components that have little impact on the outcome might be candidates for elimination or replacement.

Given the discussion thus far, it will be appreciated that, in general terms, an exemplary method, according to an aspect of the invention, includes the step of obtaining a practitioner-independent baseline outcome for a process, as at 710. A further step includes obtaining a plurality of actual outcome data points including actual outcomes for a plurality of episodes of the process, as at 708. A still further step includes, for each given one of the actual outcome data points, equating the given one of the actual outcome data points to the practitioner entity-independent baseline outcome multiplied by a plurality of unknown participating practitioner entity outcome indices for each of a plurality of participating practitioner entities, each of the participating practitioner entity outcome indices being raised to an exponent comprising a corresponding one of a plurality of unknown participating practitioner entity type indices, to obtain a plurality of equations, as per equation 400 formulated by engine 714 in step 712. An even further step includes solving the plurality of equations to obtain estimated values of the unknown participating practitioner entity outcome indices and estimated values of the unknown participating practitioner entity type indices, as per engine 716 in step 712 and FIG. 5.

In some cases, in the equating step, the participating practitioner entities are human practitioners.

In some embodiments, in the equating step, the participating practitioner entities are human medical practitioners, and, in the step of obtaining the practitioner-independent baseline outcome for the process, the process is medical treatment.

In one or more embodiments, a further step includes evaluating performance of the practitioner entities based on the estimated values of the unknown participating practitioner entity outcome indices and the estimated values of the unknown participating practitioner entity type indices. See the example in FIG. 1.

In some cases, the obtaining of the practitioner entity-independent baseline outcome for the process includes carrying out a regression wherein actual process outcomes comprise a dependent variable and with a plurality of independent variables comprising non-practitioner-entity specific factors associated with the process, as per equation 404.

In other cases, the obtaining of the practitioner entity-independent baseline outcome for the process includes simply averaging over all of the episodes with common non-practitioner-entity specific factors.

In some cases, in the equating step, at least one of the participating practitioner entities is a team of human practitioners.

In one or more embodiments, at least some of the unknown participating practitioner entity type indices have a value other than unity, and the solving step includes applying a double linear regression as per FIG. 5. In a special case, as per FIG. 6, in some cases, all of the unknown participating practitioner entity type indices are taken, a priori, as unity, and the solving step includes applying a single linear regression.

In some cases, an additional step includes obtaining an additional plurality of actual outcome data points including additional actual outcomes for a plurality of additional episodes of the process (add data to database 702 as it becomes available and repeat step 708), and repeating the equating and solving steps based on the additional actual outcomes, to update the estimated values of the unknown participating practitioner entity outcome indices and the estimated values of the unknown participating practitioner entity type indices.

As noted, in some instances, a further step includes stratifying the episodes prior to the equating and solving steps.

In some cases, a further step includes providing a system, as discussed further below. The system includes distinct software modules. Each of the distinct software modules is embodied on a computer-readable storage medium, and the distinct software modules include a database module, a multiplicative regression model formulation engine module, and a regression engine module. The step of obtaining the practitioner-independent baseline outcome is carried out at least by querying the database module, and the database module executes on at least one hardware processor. The step of obtaining the plurality of actual outcome data points is carried out by querying the database module executing on the at least one hardware processor. The equating step is carried out by the multiplicative regression model formulation engine module executing on the at least one hardware processor. The step of solving is carried out by the regression engine module executing on the at least one hardware processor.

Exemplary System and Article of Manufacture Details

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps.

Figure 8:
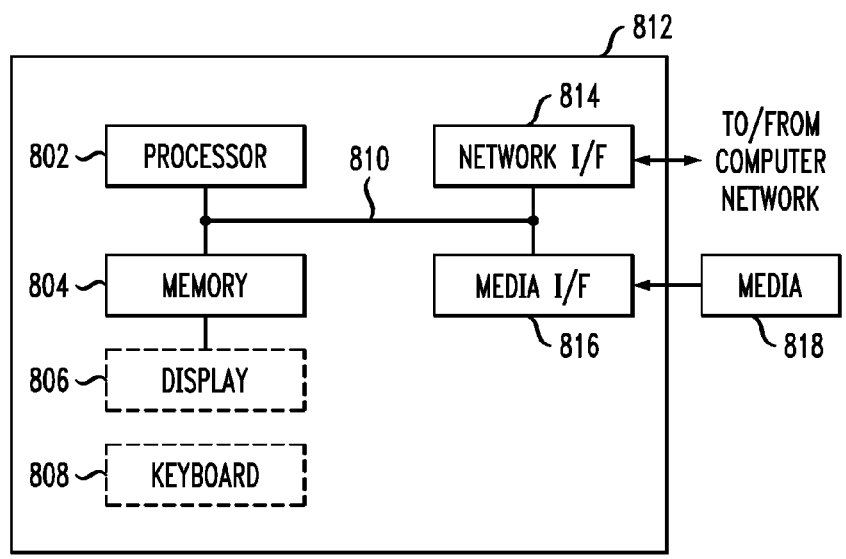
FIG. 8 depicts a computer system that may be useful in implementing one or more aspects and/or elements of the invention.

One or more embodiments can make use of software running on a general purpose computer or workstation. With reference to FIG. 8, such an implementation might employ, for example, a processor 802, a memory 804, and an input/output interface formed, for example, by a display 806 and a keyboard 808. The term "processor" as used herein is intended to include any processing device, such as, for example, one that includes a CPL (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit (for example, printer). The processor 802, memory 804, and input/output interface such as display 806 and keyboard 808 can be interconnected, for example, via bus 810 as part of a data processing unit 812. Suitable interconnections, for example via bus 810, can also be provided to a network interface 814, such as a network card, which can be provided to interface with a computer network, and to a media interface 816, such as a diskette or CD-ROM drive, which can be provided to interface with media 818.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 802 coupled directly or indirectly to memory elements 804 through a system bus 810. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 808, displays 806, pointing devices, and the like) can be coupled to the system either directly (such as via bus 810) or through intervening I/O controllers (omitted for clarity).

Network adapters such as network interface 814 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 812 as shown in FIG. 8) running a server program. It will be understood that such a physical server may or may not include a display and keyboard.

As noted, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Media block 818 is a non-limiting example. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein; by way of example and not limitation, a database module with suitable query functionality, a multiplicative regression model formulation engine module, a regression engine module, and optionally, a baseline outcome computation module. The method steps can then be carried out using the distinct software modules and/or sub-modules of the system, as described above, executing on one or more hardware processors 802. Further, a computer program product can include a computer-readable storage medium with code adapted to be implemented to carry out one or more method steps described herein, including the provision of the system with the distinct software modules.

In any case, it should be understood that the components illustrated herein may be implemented in various forms of hardware, software, or combinations thereof for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
utilizing a memory and at least one processor coupled to said memory to perform a method comprising:
obtaining a plurality of actual medical treatment outcome data points comprising actual outcomes for a plurality of episodes of a medical treatment process given to one or more patients;
obtaining a practitioner entity-independent baseline outcome for said process, wherein said practitioner entity-independent baseline outcome represents the expected outcome for a patient;
for each given one of said actual outcome data points, equating said given one of said actual outcome data points to said practitioner entity-independent baseline outcome multiplied by a plurality of unknown participating practitioner entity outcome indices for each of a plurality of participating practitioner entities, each of said participating practitioner entity outcome indices being raised to an exponent comprising a corresponding one of a plurality of unknown participating practitioner entity type indices, to obtain a plurality of equations, wherein:
the practitioner entity outcome indices comprise an indication of the performance level of a practitioner with regard to a specific outcome;
the practitioner entity type indices comprises an indication of the degree of impact of a particular practitioner type; and
solving said plurality of equations to obtain estimated values of said unknown participating practitioner entity outcome indices and estimated values of said unknown participating practitioner entity type indices to provide a Practitioner Value Assessment Tool, configured to rate and rank participating practitioners individually or in groups in their contribution to an outcome of a medical treatment process, where each individual participating practitioner has a different skill set and contributes to a different part of the medical treatment process.

2. The method of claim 1, wherein, in said equating step, said participating practitioner entities comprise human practitioners.

3. The method of claim 1, further comprising evaluating performance of said practitioner entities based on said estimated values of said unknown participating practitioner entity outcome indices and said estimated values of said unknown participating practitioner entity type indices.

4. The method of claim 1, wherein said obtaining of said practitioner entity-independent baseline outcome for said process comprises carrying out a regression wherein actual process outcomes comprise a dependent variable and with a plurality of independent variables comprising non-practitioner-entity specific factors associated with said process.

5. The method of claim 1, wherein said obtaining of said practitioner entity-independent baseline outcome for said process comprises averaging over all of said episodes with common non-practitioner-entity specific factors.

6. The method of claim 1, wherein, in said equating step, at least one of said participating practitioner entities comprises a team of human practitioners.

7. The method of claim 1, wherein at least some of said unknown participating practitioner entity type indices have a value other than unity, and wherein said solving step comprises applying a double linear regression.

8. The method of claim 1, wherein all of said unknown participating practitioner entity type indices are taken, a priori, as unity, and wherein said solving step comprises applying a single linear regression.

9. The method of claim 1, further comprising obtaining an additional plurality of actual outcome data points comprising additional actual outcomes for a plurality of additional episodes of said process; and repeating said equating and solving steps based on said additional actual outcomes, to update said estimated values of said unknown participating practitioner entity outcome indices and said estimated values of said unknown participating practitioner entity type indices.

10. The method of claim 1, further comprising stratifying said episodes prior to said equating and solving steps.

11. The method of claim 1, further comprising providing a system, wherein the system comprises distinct software modules, each of the distinct software modules being embodied on a non-transitory computer-readable storage medium, and wherein the distinct software modules comprise a database module, a multiplicative regression model formulation engine module, and a regression engine module; wherein:
said obtaining of said practitioner-independent baseline outcome is carried out at least by querying said database module, said database module executing on said at least one processor;
said obtaining of said plurality of actual outcome data points is carried out by querying said database module executing on said at least one processor;
said equating step is carried out by said multiplicative regression model formulation engine module executing on said at least one processor; and
said solving step is carried out by said regression engine module executing on said at least one processor.

12. A computer program product comprising a non-transitory computer readable storage medium having computer readable program code embodied therewith, said computer readable program code configured to cause a processor to perform a method comprising:

obtaining a plurality of actual medical treatment outcome data points comprising actual outcomes for a plurality of episodes of a medical treatment process given to one or more patients;

obtaining a practitioner entity-independent baseline outcome for said process, wherein said practitioner entity-independent baseline outcome represents the expected outcome for a patient;

for each given one of said actual outcome data points, equating said given one of said actual outcome data points to said practitioner entity-independent baseline outcome multiplied by a plurality of unknown participating practitioner entity outcome indices for each of a plurality of participating practitioner entities, each of said participating practitioner entity outcome indices being raised to an exponent comprising a corresponding one of a plurality of unknown participating practitioner entity type indices, to obtain a plurality of equations, wherein:
the practitioner entity outcome indices comprise an indication of the performance level of a practitioner with regard to a specific outcome;
the practitioner entity type indices comprises an indication of the degree of impact of a particular practitioner type; and solving said plurality of equations to obtain estimated values of said unknown participating practitioner entity outcome indices and estimated values of said unknown participating practitioner entity type indices to provide a Practitioner Value Assessment Tool, configured to rate and rank participating practitioners individually or in groups in their contribution to an outcome of a medical treatment process, where each individual participating practitioner has a different skill set and contributes to a different part of the medical treatment process.

13. The computer program product of claim 12, wherein, in said equating, said participating practitioner entities comprise human practitioners.

14. The computer program product of claim 12, further comprising computer readable program code configured to cause said processor to evaluate performance of said practitioner entities based on said estimated values of said unknown participating practitioner entity outcome indices and said estimated values of said unknown participating practitioner entity type indices.

15. The computer program product of claim 12, wherein said obtaining of said practitioner entity-independent baseline outcome for said process comprises carrying out a regression wherein actual process outcomes comprise a dependent variable and with a plurality of independent variables comprising non-practitioner-entity specific factors associated with said process.

16. The computer program product of claim 12, wherein said obtaining of said practitioner entity-independent baseline outcome for said process comprises averaging over all of said episodes with common non-practitioner-entity specific factors.

17. The computer program product of claim 12, wherein, in said computer readable program code configured to cause said processor to equate, at least one of said participating practitioner entities comprises a team of human practitioners.

18. An apparatus comprising:
a memory; and
at least one processor, coupled to said memory, and operative to:
obtain a plurality of actual medical treatment outcome data points comprising actual outcomes for a plurality of episodes of a medical treatment process given to one or more patients;
obtain a practitioner entity-independent baseline outcome for said process, wherein said practitioner entity-independent baseline outcome represents the expected outcome for a patient;
for each given one of said actual outcome data points, equate said given one of said actual outcome data points to said practitioner entity-independent baseline outcome multiplied by a plurality of unknown participating practitioner entity outcome indices for each of a plurality of participating practitioner entities, each of said participating practitioner entity outcome indices being raised to an exponent comprising a corresponding one of a plurality of unknown participating practitioner entity type indices, to obtain a plurality of equations, wherein:
the practitioner entity outcome indices comprise an indication of the performance level of a practitioner with regard to a specific outcome;
the practitioner entity type indices comprises an indication of the degree of impact of a particular practitioner type; and
solve said plurality of equations to obtain estimated values of said unknown participating practitioner entity outcome indices and estimated values of said unknown participating practitioner entity type indices to provide a Practitioner Value Assessment Tool, configured to rate and rank participating practitioners individually or in groups in their contribution to an outcome of a medical treatment process, where each individual participating practitioner has a different skill set and contributes to a different part of the medical treatment process.

19. The apparatus of claim 18, wherein said participating practitioner entities comprise human practitioners.

20. The apparatus of claim 18, wherein said at least one processor is further operative to evaluate performance of said practitioner entities based on said estimated values of said unknown participating practitioner entity outcome indices and said estimated values of said unknown participating practitioner entity type indices.

21. The apparatus of claim 18, further comprising a plurality of distinct software modules, each of the distinct software modules being embodied on a non-transitory computer-readable storage medium, and wherein the distinct software modules comprise a database module, a multiplicative regression model formulation engine module, and a regression engine module: wherein:
said at least one processor is operative to obtain said practitioner-independent baseline outcome at least by querying said database module, said database module executing on said at least one processor;
said at least one processor is operative to obtain said plurality of actual outcome data points at least by querying said database module, said database module executing on said at least one processor;
said at least one processor is operative to equate said given one of said actual outcome data points to said practitioner entity-independent baseline outcome multiplied by said plurality of unknown participating practitioner entity outcome indices for each of said plurality of participating practitioner entities, by executing said multiplicative regression model formulation engine module; and
said at least one processor is operative to solve said plurality of equations by executing said regression engine module.

22. An apparatus comprising:
a memory, and
at least one processor, coupled to said memory, and operative to provide:
means for obtaining a plurality of actual medical treatment outcome data points comprising actual outcomes for a plurality episodes of a medical treatment process given to one or more patients;
means for obtaining a practitioner entity-independent baseline outcome for said process, wherein said practitioner entity-independent baseline outcome represents the expected outcome for a patient;
means for, for each given one of said actual outcome data points, equate said given one of said actual outcome data points to said practitioner entity-independent baseline outcome multiplied by a plurality of unknown participating practitioner entity outcome indices for each of a plurality of participating practitioner entities, each of said participating practitioner entity outcome indices being raised to an exponent comprising a corresponding one of a plurality of unknown participating practitioner entity type indices, to obtain a plurality of equations, wherein:
the practitioner entity outcome indices comprise an indication of the performance level of a practitioner with regard to a specific outcome;
the practitioner entity type indices comprises an indication of the degree of impact of a particular practitioner type; and
means for solving said plurality of equations to obtain estimated values of said unknown participating practitioner entity outcome indices and estimated values of said unknown participating practitioner entity type indices to provide a Practitioner Value Assessment Tool, configured to rate and rank participating practitioners individually or in groups in their contribution to an outcome of a medical treatment process, where each individual participating practitioner has a different skill set and contributes to a different part of the medical treatment process.

* * * * *